US00PP36035P2

(12) United States Plant Patent
Hansen

(10) Patent No.: US PP36,035 P2
(45) Date of Patent: Jul. 23, 2024

(54) ***COREOPSIS* PLANT NAMED 'CREAMY CALICO'**

(50) Latin Name: *Coreopsis verticillata*
Varietal Denomination: Creamy Calico

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,666

(22) Filed: Dec. 15, 2023

(51) Int. Cl.
*A01H 5/02* (2018.01)
*A01H 6/14* (2018.01)

(52) U.S. Cl.
USPC ..... Plt./417
CPC ..... *A01H 6/14* (2018.05)

(58) Field of Classification Search
USPC ..... Plt./417
CPC ..... A01H 6/14; A01H 5/02
See application file for complete search history.

*Primary Examiner* — Keith O. Robinson

(57) ABSTRACT

A new and distinct Threadleaf *Coreopsis* plant, *Coreopsis verticillata* plant named 'Creamy Calico', with narrowly-linear, deeply-dissected, typically 3 to 6-lobed foliage of bright-green, numerous flowers of soft yellow ray florets with large deep maroon centers over a prolonged flowering season from mid-June until late summer. The new plant is useful for landscaping as a specimen plant, en masse, in containers, and as a cut flower.

1 Drawing Sheet

Botanical designation: *Coreopsis verticillata.*
Cultivar denomination: 'Creamy Calico'.

STATEMENT REGARDING PRIOR DISCLOSURES UNDER 37 CFR 1.77(b)(6)

The first public disclosure of the claimed plant, in the form of a website to the public and email release to customers, was made by Walters Gardens, Inc. on Dec. 1, 2023. Walters Gardens, Inc. obtained the new plant and information about the new plant directly from the inventor. The first offer for sale of the new plant was on Jan. 9, 2023, by Walters Gardens, Inc. No plants of *Coreopsis* 'Creamy Calico' have been offered for sale or sold, in this country or anywhere in the world, nor has any disclosure of the new plant been made, more than one year prior to the filing date of this application, and such sale or disclosure within one year was either derived directly or indirectly from the inventor.

BACKGROUND OF THE PLANT

The present invention relates to the new and distinct Threadleaf *Coreopsis* herein also referred to as *Coreopsis* 'Creamy Calico', by the cultivar name, 'Creamy Calico', or as the new plant. The new plant was a cross by the inventor on Aug. 1, 2018, between the proprietary unreleased hybrid known only by 17-11-xx (not patented) crossed with the proprietary unreleased hybrid known only by 17-10-10 (not patented) in the research facility of a wholesale perennial nursery based in Zeeland, MI, USA. The single seedling identified by breeder code 18-63-2 was then isolated and compared in subsequent years to other *Coreopsis* and subsequently found to be different from all cultivars known to the discoverer.

Asexual propagation at the same nursery in Zeeland, MI, USA by cuttings has shown 'Creamy Calico' to be stable and reproduce true to type in successive generations since spring 2019.

SUMMARY OF THE PLANT

*Coreopsis* 'Creamy Calico' has not been observed in all possible environmental conditions. The phenotype may vary slightly with changes in environments such as light intensity, fertility, water availability, etc. without, however, any variations in genotype.

*Coreopsis* 'Creamy Calico' is distinct from all cultivars known to the inventor in the following traits:

1. Narrow foliage with compact height and dense habit.
2. Heavy flowering of soft yellow ray florets with large deep maroon centers.
3. Flowers are produced tightly and densely above the bright-green thin foliage.
4. Long flowering period beginning with concentration in mid-June and continuing until late summer in Michigan.

The new plant is known by the inventor to be most similar to the cultivars: 'Sassy Saffron' U.S. Plant Pat. No. 31,391, 'Curry Up' U.S. Plant Pat. No. 28,521, 'Red Hot Vanilla' U.S. Plant Pat. No. 30,909, 'Route 66' U.S. Plant Pat. No. 20,609, 'Electric Avenue' U.S. Plant Pat. No. 24,688, 'Broad Street' U.S. Plant Pat. No. 24,598 and 'Red Chiffon' U.S. Plant Pat. No. 27,528.

'Sassy Saffron' has a similar habit, but the ray florets have a smaller center reddish eye and the outer portion has a slightly deeper lemon-yellow. 'Curry Up' has ray florets that are deeper golden on the outside and lighter reddish in the center. 'Red Hot Vanilla' has ray florets that are cream-colored on the outside and dark red in the center. 'Route 66' has ray florets that are paler yellow on the outside and lighter reddish in the center with flecking or blotching toward the apex. 'Electric Avenue' has ray florets that are narrower and solid yellow without the dark red center. 'Broad Street' has lighter reddish ray florets with just a speckling of the yellow toward the apices. 'Red Chiffon' has ray florets that are also deeper yellow on the outside and not as dark burgundy in the inside.

The female has ray florets with a red center and yellowish coloring on the edge. The male parent has solid reddish ray florets.

BRIEF DESCRIPTION OF THE DRAWINGS

The color drawings illustrate the overall characteristics of *Coreopsis* 'Creamy Calico' as three-year-old plants are grown in a full-sun trial garden in Zeeland, Michigan. The colors are as true as reasonably possible given the technology available. The color values may vary slightly depending on light intensity and quality.

DETAILED BOTANICAL DESCRIPTION

Figure 1:
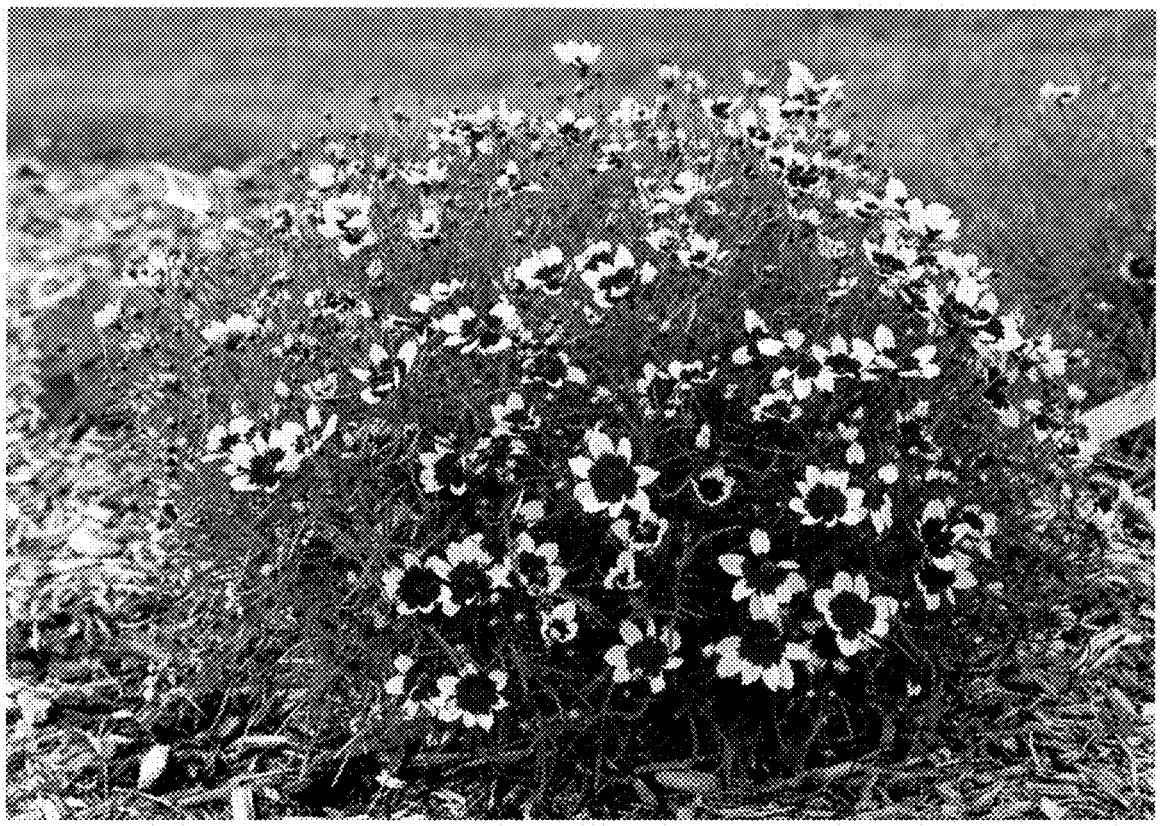
FIG. 1 shows three new plants in a landscape environment.
Figure 2:
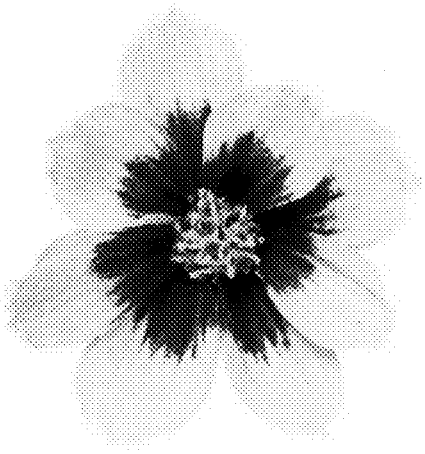
FIG. 2 and FIG. 3 shows a close-up of the flowers of the new plant with the young flower on the left and the more mature flower on the right.
Figure 3:
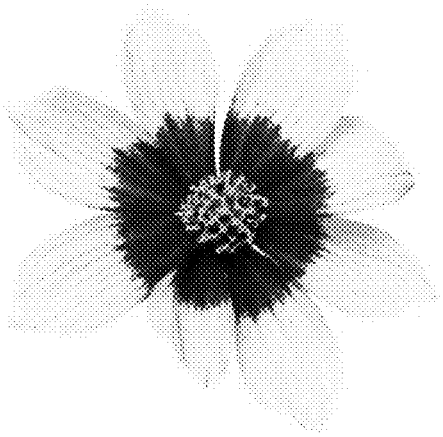

The following description is based on a two-year-old plant grown in a full-sun trial garden and also a one-year-old plant grown in a partially-shaded greenhouse in Zeeland, Michigan, USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: The female or seed parent is the proprietary hybrid 17-11-xx; the male or pollen parent is the proprietary hybrid 17-10-10;

Asexual propagation: Cuttings, about 10 to 14 days to initiate roots; time to finish as #1 field grown size about 9 months;

Plant habit: Dense axillary branches; rounded, herbaceous perennial mound; up to 43 cm wide and 45 cm tall;

Branches: Up to 8 per stem, lower branches compound; glabrous, cylindrical; to 24 cm long and 2 mm diameter; emerging at an angle about 45 degrees above horizontal;

Branch color: Nearest RHS 137B;

Leaves: Opposite; entire; variable, linear to irregularly tri-lobed or penta-lobed, deeply dissected to midrib; acute apex; base attenuate; sessile; glabrous;

Leaf size: To 7 cm long and 5.8 cm wide, average about 5.4 cm long and 4.2 cm wide; side lobes at about a 45° to 60° angle to center lobe, center lobe to 4.0 cm long and 3 mm across; center lobe to 3.5 cm long and 2 mm wide;

Leaf color: Young expanding leaves adaxial and abaxial nearest RHS 146B; mature leaves adaxial between RHS NN137A and RHS NN137B, abaxial between RHS 137A and RHS NN137B;

Veins: Pinnate; only abaxial midrib obvious;

Abaxial midveins color: Adaxial between RHS NN137A and RHS NN137B, abaxial nearest RHS 137A;

Inflorescence: Radiate; composite consisting of ray and disk florets; on terminal branches; about 3.5 cm diameter, about 1.2 cm tall from lower involucral bracts to top of disk florets; attitude upright to outwardly; to about 80 inflorescences per stem;

Flower fragrance: Not detected;

Phyllary: Two distinct whorls; an outer or lower set consisting of about eight, salient, glabrous adaxial and abaxial, with acute apex, lanceolate, truncate base, to about 5 mm long and 1 mm wide at base; an inner or upper set pressed tight against ray florets, eight to ten in number, to about 6 mm long and about 3 mm wide, ovate, acute apex and rounded truncate base;

Phyllary color: Lower set between RHS NN137B and RHS 137A both adaxial and abaxial; upper set between RHS 152A and RHS 146A in the central portion of both adaxial and abaxial; marginally translucent and nearest RHS 153A both adaxial and abaxial;

Flowering period: Early summer until late summer, for about 10 weeks;

Flower longevity: 4 to 6 days on the plant or as a cut flower;

Inflorescence buds: One to two days before ray floret flattening-terete; flat top and rounded base; 6 mm wide and 14 mm tall;

Inflorescence bud color: Exposed ray florets distally nearest RHS 2A with exposed eye zone having an undertone of nearest RHS N186C;

Peduncle: Cylindrical; glaucous; upright attitude; thin, wiry, stiff, strong; to about 1 mm diameter at the base and about 8 cm long before capitulum; about 8 ray florets 35 to 40 disk florets per peduncle;

Peduncle color: Between RHS 137A and RHS 137B;

Stem: Cylindrical; fluted; to about 30 cm long, 5 mm diameter at the base and 2.5 mm diameter below last branched peduncle; about seven nodes, average internode spacing about 4.3 cm; spacing increasing distally;

Stem color: Between RHS 137A and RHS 137B;

Node: Swollen to about 5 to 6 mm across;

Node color: Same as surround stem, nearest RHS 137B;

Bristles: Thin; lustrous; slightly arcuate; about 4 mm long and 0.5 mm across; color distally nearest RHS N163B and proximally nearest RHS 163A;

Ray florets: Imperfect; sterile; zygomorphic; typically, 8 per inflorescence;

Ray floret ligule: Oblong elongate; glabrous adaxial and adaxial; apex typically two-notched; margin entire; base claw, narrowly cuneate to attenuate; opening flat to form 180° face with other ray florets; parallel-veined; to about 17 mm long and about 7 mm wide; basal corolla claw about 1 mm long and about 0.7 mm diameter;

Ray floret color: Adaxial basal 1 mm nearest RHS 151D, next proximal half nearest RHS N186C, distal half nearest RHS 4B when first flattened and lightening to between RHS 8D and RHS 8C when mature; abaxial basal 2 mm nearest RHS 151D, next proximal half nearest RHS 161A, distal half nearest RHS 4B when first flattened and lightening to between RHS 8D and RHS 8C when mature;

Disk florets: About 35 to 40 per capitulum; consisting of four tepals, staminal tube and pistil; size about 7 mm long by 1 mm wide at apex and about 0.7 mm diameter at base;

*Tepals*.—Four; 3 mm long and 1 mm wide, corolla fused in the basal 2 mm, acute apex.

*Tepal color*.—Adaxial nearest RHS 183A in distal 1 mm, abaxial distal 1 mm nearest RHS 163A at margin, center nearest RHS 166A, and basal 1 mm nearest RHS 161A.

*Staminal tube*.—Made up of four fused anthers, about 3.5 mm long.

*Anther*.—About 2 mm long, nearest RHS N186A.

*Filament*.—Four; cylindrical; about 1.5 mm long and 0.1 mm diameter; color nearest RHS 8C.

*Pollen*.—Abundant; minute; color nearest to RHS 15A.

*Style*.—Cylindrical; about 4 mm long and 0.2 mm diameter; nearest RHS 21C.

*Stigma*.—Bifid and cochleate as it matures; about 1 mm long and 0.3 mm diameter; color nearest RHS 15A.

Seed: Has not been observed;

*Coreopsis verticillata* 'Creamy Calico' is tolerant of winter temperatures as low as −20° C. and summer temperatures as high as 40° C. Once established it is also tolerant of dry summer conditions but does best with ample moisture and good drainage. It is not known to be tolerant or susceptible to diseases and pests that are common to other *Coreopsis* cultivars.

I claim:

1. A new and distinct cultivar of *Coreopsis* plant named 'Creamy Calico' as described and illustrated.

* * * * *